(12) United States Patent
Beck et al.

(10) Patent No.: US 7,591,584 B2
(45) Date of Patent: Sep. 22, 2009

(54) TEMPERATURE-EXPANSION INDICATOR FOR SIDING PANELS

(75) Inventors: David H. Beck, Jackson, MI (US); Robert D. Shaw, Parma, MI (US); David J. Stucky, Grass Lake, MI (US)

(73) Assignee: CerainTeed Corporation, Valley Forge, PA (US)

( * ) Notice: Subject to any disclaimer, the term of this patent is extended or adjusted under 35 U.S.C. 154(b) by 728 days.

(21) Appl. No.: 11/201,722

(22) Filed: Aug. 10, 2005

(65) Prior Publication Data

US 2006/0078035 A1 Apr. 13, 2006

Related U.S. Application Data

(62) Division of application No. 10/700,994, filed on Nov. 4, 2003, now Pat. No. 6,939,036.

(51) Int. Cl.
*G01K 5/00* (2006.01)
*G01N 25/34* (2006.01)

(52) U.S. Cl. .......................... 374/55; 374/100; 374/187

(58) Field of Classification Search ............... 374/6, 374/43–57, 137, 29, 208, 141, 187, 100, 374/210
See application file for complete search history.

(56) References Cited

U.S. PATENT DOCUMENTS

| | | | |
|---|---|---|---|
| 1,638,425 A | 8/1927 | Whittemore | |
| 2,820,296 A * | 1/1958 | Fabian | ........................ 33/704 |
| 3,197,335 A * | 7/1965 | Leszynski | ................... 338/308 |
| 3,665,756 A * | 5/1972 | Russell | ........................ 73/766 |
| 3,938,889 A | 2/1976 | McKinnis | |
| 4,054,049 A | 10/1977 | Egger | |
| 4,923,307 A | 5/1990 | Gilmore et al. | |
| 5,009,512 A | 4/1991 | Lessi et al. | |
| 5,052,121 A | 10/1991 | Wachtler | |
| 5,161,891 A | 11/1992 | Austill | |
| 5,511,321 A | 4/1996 | Nelle | |
| 5,918,981 A | 7/1999 | Ribi | |
| 6,019,506 A * | 2/2000 | Senda | ......................... 374/55 |
| 6,055,786 A * | 5/2000 | Hubbard et al. | ............... 52/409 |
| 6,120,179 A | 9/2000 | Houser et al. | |
| 6,386,756 B1 | 5/2002 | Rice | |
| 6,544,614 B1 | 4/2003 | Huffer et al. | |
| 6,604,854 B1 | 8/2003 | Limburg et al. | |
| 6,672,759 B2 | 1/2004 | Feger | |
| 6,973,837 B2 * | 12/2005 | Barnett | ........................ 73/765 |
| 7,253,740 B2 * | 8/2007 | Cain et al. | .................. 340/596 |

FOREIGN PATENT DOCUMENTS

| | | |
|---|---|---|
| DE | 10007540 A1 | 9/2001 |
| JP | 58162821 A | 9/1983 |
| SU | 1024697 A * | 6/1983 |

\* cited by examiner

*Primary Examiner*—Gail Verbitsky
(74) *Attorney, Agent, or Firm*—Duane Morris LLP

(57) ABSTRACT

A temperature indicator for a siding panel senses panel temperature and indicates on a graphic scale the corresponding effect of thermal expansion over differences in temperature. The temperature indicator can be various forms of contact thermometer, temperature strip or sensor and can be integral or temporarily affixed during installation or for later assessment for correct panel gapping. The indicator shows how closely the edge of the panel can be placed to an adjacent surface while avoiding interference over a range of thermal expansion temperatures.

20 Claims, 4 Drawing Sheets

TEMPERATURE-EXPANSION INDICATOR FOR SIDING PANELS

CROSS REFERENCE TO RELATED APPLICATION

This is a division of application Ser. No. 10/700,994, filed Nov. 4, 2003, now U.S. Pat. No. 6,939,036.

BACKGROUND OF THE INVENTION

The invention relates to methods and apparatus for installation of components such as building components, especially exterior-finishing panels such as polymer siding, which components are subject to expansion and contraction with changes in temperature.

PRIOR ART

Siding products for facing exterior building walls can resemble traditional wooden clapboards, cedar shakes and the like and are available in durable low-maintenance materials such as aluminum and various polymers. Simulative modern siding panels often are made to resemble traditional wood siding materials. A traditional wooden siding material might be installed in overlapped tiers or courses, for example single horizontally elongated clapboards or single rows of discrete single shingles, placed adjacent to one another and individually nailed. Modern siding materials also are installed in overlapping courses, but each course of the siding panel material can simulate two or more overlapped courses of traditional materials such as clapboards or shingles.

In the case of simulated shingles or cedar shakes, each integral siding panel simulates at least one row of laterally adjacent shingles, and usually simulates two or more courses that appear to overlap vertically. The siding panel is supplied in convenient lengths for handling and installation, for example four or eight or twelve feet. Thus, in the direction of elongation, a siding panel might represent one or more clapboards, or perhaps a few simulated shingles or as many as several dozen shingles. The siding panel typically simulates an installed array of traditional siding elements such as boards or shingles. Therefore, the siding panel reflects the shape of the boards or shingles and also the gaps between them, and their traditional installation as overlapping tiers or courses.

More or less complicated joints affix abutting and/or overlapping edges of panels to other adjacent panels, both end to end and in overlapped courses. A simple joint may involve at least a slight overlap. A more complicated joint can have inter-engaging shapes that fit together to bridge the joint. A combination of overlap and engagement is advantageous to ensure coverage of the substrate (the building wall), for example with one panel having a web that extends flat along the substrate for a short distance under the other. Various types of joints are known.

One object of such paneling is to cover the substrate. Another object is attractively to simulate traditional building materials such as clapboards or shingles. It is highly desirable to avoid gaps at which the substrate is visible. It is also desirable to conceal joints between siding panels. One potentially effective way to conceal the joints between panels is to structure them to resemble gaps between traditional siding elements such as the gaps between installed shingles. This is complicated by the fact that the siding panels need freedom to expand and contract relative to the substrate, with changes in temperature.

The siding panels are hung in overlapping courses. Proceeding from a point of low elevation, for example, a panel is positioned and nailed to the building by passing fasteners (e.g., nails) through the top edge of the panel, normally through a nailing strip having holes to receive the fasteners. The next upper course overlaps and conceals the nailing strip along the top edge of the next lower course. As the panels are installed, each section of paneling is joined to the next adjacent panel(s) on the same level or course. Locking structures or reference ridges can be provided to affix the bottom edge of the upper course correctly relative to the overlapped lower course, and butt joint structures can affix panels end-to-end in the direction of their elongation. However, there must be clearance for the panels to expand without interference, and sufficient overlap or depth of joint engagement so that when the panels contract, they remain adequately attached.

Thermal expansion is a particular issue with elongated materials and materials that have a relatively large index of thermal expansion (such as vinyl and other polymeric materials) compared to a building wall as a substrate. Apart from differences in index of thermal expansion, there is differential heating. The siding is exposed to the elements and is more prone to temperature cycling than the building substrate that is covered by the siding panel, and thus shielded from heating and cooling influences. Passing sunlight, for example, can cause a very substantial but temporary temperature increase that may be limited to a particular building wall or even a particular exposed section of a wall.

In order to allow for thermal expansion, siding is hung or suspended from the substrate or building structure so as to permit relative displacement. Clearance is needed in the direction of elongation of the panels (in butt joints and at the ends of courses). Clearance also is needed in the perpendicular direction if there is an associated overlap joint between courses. Typically the panels are elongated horizontally (although not necessarily so), so accommodations are made in particular for the panels to expand or shrink in that direction. For example, the end-to-end butt joints between panels on a course are structured to permit a range of engagement depths while maintaining some overlap. Trim moldings can be provided to conceal a gap between the panels and inside and outside corners and at framing window or door openings. The gap grows smaller and larger with heating and cooling of the siding panels. The moldings have flanges that extend over the gap to cover the ends of the panels.

In order to permit expansion, the panels are hung using loosely affixed nails or other fasteners, at least some of which are received in slots rather than round holes, the slots being elongated in the direction of panel elongation. For example, each panel may have a single round hole at a midpoint for receiving a nail that sets a reference point, e.g., at the center of the panel, which point will become fixed relative to the wall when the fastener is set in place. Proceeding outwardly from the reference point, the nails or other fasteners are received in slots. The installer typically places each nail at a space from both opposite ends of slot and does not set the nail so deeply that the nail head bears against the siding. As the panel expands or contracts with changes in temperature, elongation or contraction moves the panel carrying the slots, relative to the fixed nails or other fasteners.

If appropriate attention is not paid to thermal expansion issues, a siding project can fail. Nails or other fasteners that are wrongly placed can encounter an end of a mounting slot and become displaced. If a panel is blocked from expanding with heat, the panel may bow outwardly. A bowing panel can lift the nails that hold the panel in place. An expanding panel can exert pressure that disturbs the position of trim moldings or other panels, or may cause a joint to pop apart.

Expansion and contraction occur repeatedly over time with cycles of heating and cooling. Back and forth pressure can detach a reference fastener. If the expansion and contraction of a set of one or more contiguous panels is applied to the same point (for example the expansion and contraction of several locked-together panels adds), a visible gap can open and may even expose the substrate.

Installation instructions provided by siding manufacturers provide information on how exactly to hang siding so as to accommodate thermal expansion and contraction. Nevertheless, it is sometimes difficult for the installer to comply with such instructions because the correct installation procedure depends on the temperature of each individual panel at the time of its installation.

The installer naturally has at least a general idea about the ambient temperature in which he/she is working and might estimate the air temperature reasonably accurately. However, the ambient temperature varies over time, and the local temperature of the panels varies. In moving the panels around, e.g., from vehicle to a ready area to their final placement on the building, the temperature of the panels can change substantially. Particularly when panels are placed on the building, possibly in the sun or in the shade, temperature variations occur that are specific to a relatively isolated area and may vary substantially from ambient air temperature. What is needed is a way to determine and respond to the temperature of the siding panels individually at the time of installation.

There are various forms of temperature measurement devices available, but most measure ambient air temperature. It would be possible to provide a surface temperature sensor such as an optical pyrometer to measure the temperature of an isolated area such as a spot on a given panel. However the measurement apparatus is expensive and it is unwieldy to require the installer to deploy such an apparatus to take a reading on each panel when installing the panel. Therefore, the installer generally assumes that the panels are approximately at the ambient temperature of the air. This can cause expansion/contraction problems that arise during and after installation.

It is normally the duty of the installer to space the siding panels in view of the ambient temperature, according to specific instructions. The installation instructions, for example, may contain a table of panel spacing versus temperature, and typically instruct that all joints between defined points on endwise abutted panels be gapped at a distance that is determined as a function of temperature. In anticipation of the expansion/contraction performance of the panels, when the ambient temperature is high, only small gaps are provided between edges of abutting panels that may interfere because the panel is not expected to expand much more. If the ambient temperature is low, then larger gaps should be provided. The gap should be large enough never to close completely at the highest temperature encountered, which might cause the respective edges to come into contact and exert a force. Conversely, the gap should be small enough so as not to gap visibly, or worse yet to expose the substrate, at the coldest temperature encountered.

Warranty claims are made from time to time because bowing occurs, joints open or fasteners become detached. Although such claims might properly be made if there is a problem with the siding, or perhaps with the instructions for hanging the siding, it is likely that the root of the problem is an inadvertent failure to comply with instructions respecting installation at a particular temperature. However, when investigating a warranty claim made long after an installation, it is typically not possible to determine the precise temperature conditions at the time of installation. Some technique is needed to assist the installer in dealing with temperature issues and pertinent temperature variations. It would be highly desirable if that technique also could provide a way to refer back to the time of installation, so as to determine whether an installation at a previous time and under possibly different temperature conditions, was or was not accomplished in keeping with the manufacturer's installation instructions.

A very high quality panel installation job requires a good deal of attention to precise placement of the panels. If the installation is not precise, the gaps between siding panels can be unduly visible. If the installation is done correctly, then the gaps are all about the same width at a given temperature. Preferably, in siding that simulates shingles or cedar shakes, the gaps between simulated shingles or shakes on two panels that abut endwise at a joint are not visibly different from the gaps between simulated shingles at an intermediate area of an integral siding panel. The gaps between simulated shingles are small, for example, 0.125 or 0.250 inches.

The decorative gap between simulated shingles is on the same order of magnitude as the variation in the dimensions of a nominal length of vinyl panel during routine temperature cycling. If the installer eyeballs the spacing between panels to make the gap between panels about the same as the gap between the shingles, interference may occur (the inter-panel gap may close completely) at high temperatures.

For example, if the coefficient or index of thermal expansion of vinyl siding material is typically about $3.5 \times 10^{-5}$ in./in./° F. and the panel is six feet long (72 inches), the panel expands in length by about 0.0025 inch per degree F. Assuming that such a panel is 72 inches long at 0° F., it is 72.10 inches at 40° F. and 72.25 at 100° F. The ambient air outside a building might be 40° F., but at the same time the surface temperature of siding in direct sun on the south-facing side of a building might easily be 100° F. Inasmuch as the width of the gap between simulated shingles is of approximately the same width as the extent of thermal expansion, and thermal expansion and contraction occur regularly, problems can arise.

One way to deal with expansion problems is to limit the panels to a relatively short length. This complicates installation compared to installing longer panels. What is needed is a way to install siding in a manner that is precisely tied to the temperature of the particular piece of siding at the time of installation. Assuming that such a need is met, what is also needed is a way to determine whether the installation is correct, even if the temperature has later changed.

SUMMARY OF THE INVENTION

According to an inventive aspect, these problems are resolved by providing an integral or temporarily deployed temperature sensor for determining actual current panel temperature, independent of ambient air temperature. In addition, a gap spacing indicator is associated with the panel joint. The temperature sensor can have a readout that is laid out spatially to correspond to the expansion of the siding panel at the temperature to which the sensor responds, the scale of the temperature readout thus providing a gap spacing indicator wherein thermal expansion characteristics are read out as a function of temperature. Alternatively, a temperature sensor can provide a numeric sensed panel temperature value and the corresponding gap is found on a separately associated temperature-versus-spacing graphic pattern or like reference. By placing the temperature sensor against the panel (or affixing the sensor or providing it integrally), the installer or a troubleshooter subsequently can determine the correct gap at the actual sensed panel temperature, for correct installation and/or as a technique to assess the accuracy of panel mounting with respect to thermal expansion clearance issues, at some later time and/or temperature.

Thus according to one aspect, the invention provides a siding panel and a temperature sensor and included or associated indicator that correspond in their temperature responses, one by expansion and the other by indicating a position or gap that corresponds to the expansion characteristic of the panel at the associated temperature.

The siding panel has a thermal expansion characteristic by which the material of the panel expands and contracts with temperature. That is, the panel expands (or contracts) by a predetermined distance, per unit of material length, per unit of temperature difference. The temperature sensor is arranged to indicate the expansion distance between at least two temperatures and preferably over an expected temperature range. The indication can be presented on or parallel to an axis of elongation of siding panels between joints, for example horizontally between panels that are butt jointed with adjacent panels on each course, over a reference distance. The reference distance can extend between an edge of the panel at a butt joint, which edge may interfere with an adjacent panel if improperly gapped, and a spaced point of reference. The spaced point of reference can be the opposite end of the panel, but also can be a fixed point such as a centrally located fastener reception hole.

The temperature indicator has a temperature responsive indicating scale spanning a distance with indications of gaps at least for two temperatures, and preferably is laid out to encompass the full range of expected temperatures to which the siding may be exposed, showing the effect of thermal expansion on the relative position of an edge or similar reference point. The temperature indicating spatial positions are placed to correspond to the expansion and contraction characteristics of the panel.

According to another aspect, the thermal sensor used to provide this corresponding indication of temperature and expansion can include a chemical temperature indicator such as a thermotropic composition, an optical temperature indicator such as a liquid crystal indicator or thermochromic element, with zones that change opacity or some other visual characteristic at given temperatures, an expansion material or fluid, a bimetal indicator or another temperature measurement device with an output that can be spatially presented so as to correspond to the temperature expansion of a material having the necessary nominal temperature expansion characteristic over a predetermined useful span of material length.

The temperature indicator, for a particular material or siding panel, senses the material temperature of the panel and indicates on a graphic scale or is referenced to a separate graphic scale, wherein the corresponding effect of thermal expansion at such temperature is represented as an edge position used to set a gap. As the temperature differs, a different edge position is identified to account for the subsequent difference in temperature and thermal expansion of said particular material over a given length. The temperature sensor and corresponding position indication scale enable highly precise mounting in the case of a siding panel or highly precise positioning in other applications.

The temperature indicator can be of various forms that provide either a spatial indication of expansion or a numeric indication that is convertible to a spatial indication, for example by pitching the temperature scale to represent material expansion or providing a numeric readout referenced to a spatial scale plotting temperature to expansion. A contact thermometer, temperature strip or similar contact sensor can be provided integrally with the panel, or temporarily affixed or held in place during installation or later assessment for correct panel gapping or mounting. The indicator shows how closely the edge of the panel can be placed to an adjacent surface while avoiding interference over a range of thermal expansion temperatures. In a post-installation assessment, the indicator also shows whether the spacing during installation, which may have been at a different temperature, was correct.

BRIEF DESCRIPTION OF THE DRAWINGS

The foregoing features and advantages of the invention, as well as other aspects and routine extensions of the invention, are apparent from the following detailed description of examples and preferred embodiments, to be considered together with the accompanying drawings, wherein the same reference numbers have been used throughout to refer to the same functioning parts, and wherein:

FIG. 7 is a perspective view showing that the invention is applicable to other forms of temperature indicators such as expansion materials, bimetals and the like.

DETAILED DESCRIPTION

Figure 1:
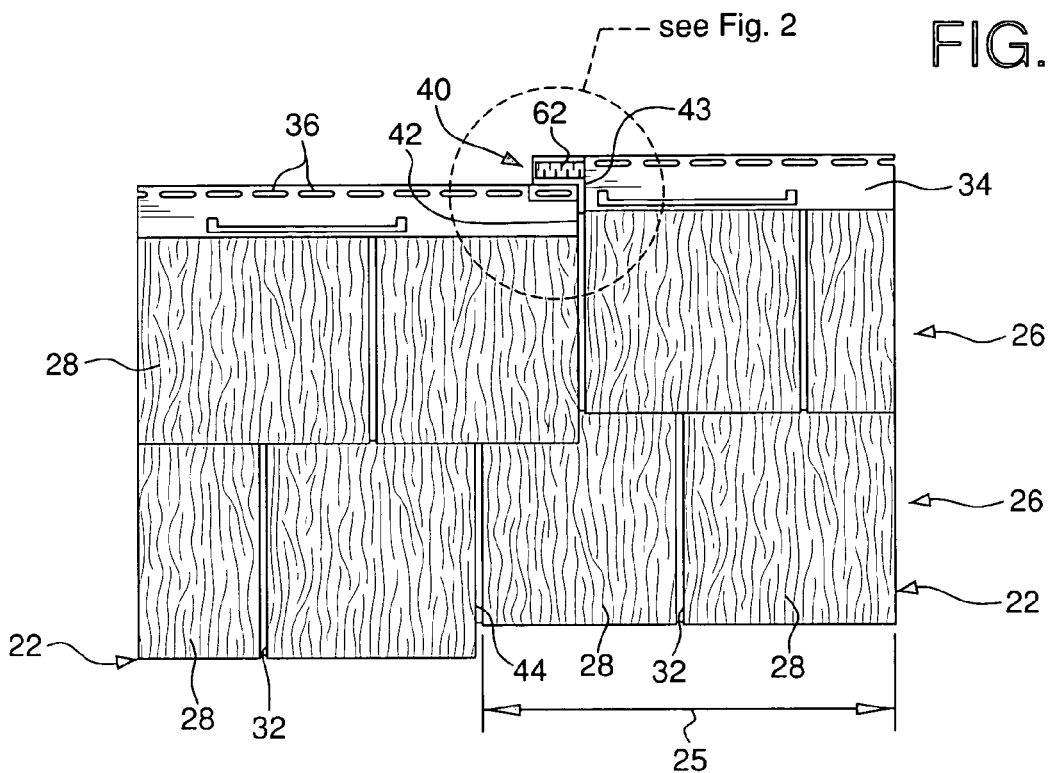
FIG. 1 is an elevation view showing the present invention applied to the assembly of two siding panel sections, namely with a temperature indicator laid out to correspond with the thermal expansion properties of the siding panel, and useful for precise panel spacing and assessment.

A number of exemplary embodiments of the invention are described herein with reference to the drawings. These embodiments are examples intended to demonstrate aspects of the invention in different forms or separately. Not all the aspects are required in all embodiments of the invention, and the illustrated embodiments should be regarded as exemplary rather than limiting.

For example, the illustrative embodiments discussed concern building siding materials of the sort typically installed in horizontally elongated courses on external building surfaces that are vertical and flat. The nature of the installation surface and whether or not the courses are elongated horizontally, are subject to variation. For example, the surface could be sloping (such as a roof) or curved. The direction of elongation of the panels could be vertical or inclined instead of horizontal. The application could be an exterior or interior building application or an application that is not related to a building per se. Therefore, in this description, terms denoting relative directions and orientations such as "lower," "upper," "horizontal," "vertical," "above," "below," "up," "down," "top" and "bottom" should be construed to refer to the orientation as then being described or as shown in the drawing under discussion.

Terms concerning attachments, coupling and the like, such as "connected" and "interconnected," refer to a relationship wherein elements are integral parts of a whole, or are secured or attached to one another either directly or indirectly through intervening structures, as well as both movable or rigid attachments or relationships, unless expressly described otherwise or as apparent in view of the described functions of such elements.

Referring to FIG. 1 two siding panels 22 are shown. The panels 22 can be of various sizes, shapes and types, for example representing cedar shakes, wood shingles, clapboards or other materials. Each siding panel 22 encompasses an area, namely a distance over a span of horizontal elongation in this example 25, and a span of height. In the example shown, the siding panels 22 are embodied to represent two courses 26 of traditional wooden material such as cedar shakes 28. Each panel 22 is integrally formed by extrusion or injection molding, for example of polypropylene, vinyl or another material. Each panel 22 represents several individual shakes or shingles 28, separated by representations of inter-shingle gaps 32 that actually are variations in surface height as opposed to through-gaps between portions of the integral panel material (although actual through-gaps would also be possible. The simulated shingles 28 in the courses 26 shown are mounted by means of nails or other fasteners (not shown) passed through a nailing strip 34 along the top edge.

The panels 22 are subject to differential thermal expansion relative to the building wall that they cover (not shown). In order to permit each panel 22 to expand and contract relative to the building wall, the nailing strip 34 has elongated openings or slots 36 that receive the fasteners and permit some movement of the siding relative to the wall during thermal expansion and contraction.

The two panels 22 are shown during a phase of assembly or mounting in FIG. 1. The panels 22 meet at a butt joint 40. Specifically, the two panels 22 have edges 42, 43 that are brought nearly into abutment at the joint 40, spaced by a joint gap 44 that varies with expansion and contraction. Gap 44 occurs between the extreme edge 42 of the endmost simulated shingle 28 of the overlapping panel 22 and the presented visible edge 43 of the endmost shingle 28 of the adjacent panel 22. This adjacent panel has an apron or flap 52 that underlies the joint 40.

It would be advantageous for appearance purposes if the gap 44 between the integral panels 22 (namely the gap 44 between their endmost shingles 28), was of substantially the same width as the gap between the simulated shingles 28 on each integral panel 22. If the inter-panel gap 44 is indistinguishable from the intra-panel gaps between shingles 28, the distinction between the panels 22 is concealed. The panels as mounted across joint 40 then more closely resemble an array of shingles that are not divided into separate panels 22. The masking effect can be enhanced by using a random variation of gap widths between simulated shingles 28. It is not possible to make the inter-panel and intra-panel gaps equal because the inter-panel gaps 44 vary with differences in thermal expansion of panels 22. The width of the gap 44 between edges 42, 43 of the simulated shingles across the butt joint varies with temperature by a much greater extent than the simulated intra-panel gaps between the integrally connected simulated shingles 28.

Figure 2:
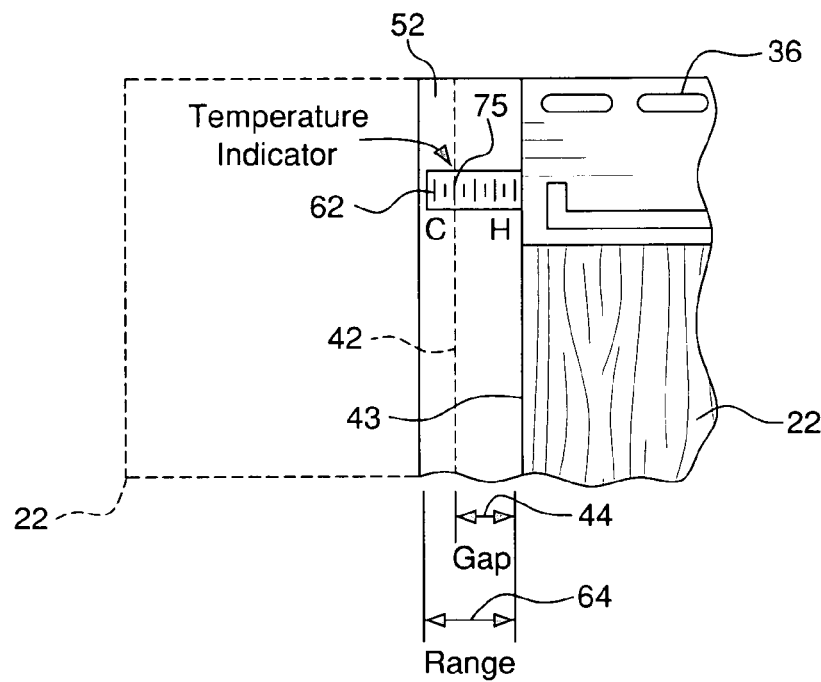
FIG. 2 is a detailed elevation view showing the region of the gap between one panel and a next panel, the latter panel being shown by a broken line, and the temperature indicator having a visible mark indicating the current temperature of the siding panel.

As shown in FIG. 1 and in more detail in FIG. 2, the panels 22 have butt joints 40 that partly overlap. The left edge of one panel 22 is structured to join with the right edge of another panel 22 in each case. Insofar as it is necessary to trim the panels to fit an area on a wall to be sided, such as an area between inside and outside corners, window frames, door jambs and the like, all the cuts are made at a distance from any joint 40. The cut ends are concealed by moldings and covering flanges at the ends of each course. The joints 40 between panels 22 in visible areas are made as shown by using complementary panel structures that are intended to appear the same as gaps between simulated shingles 28.

One of the panels 22 at a joint 40 has an underlying apron or flap 52 that lays against the substrate (such as a building wall—not shown). The other of the panels 22 at the joint 40 extends over the apron or flap 52 so as to position the endmost simulated shingle edge near to the corresponding end most edge of the next adjacent shingle and panel across the butt joint 40.

To provide sufficient temperature expansion clearance, it is necessary that the joint 40 contain a gap 44 between edges 42, 43, at all but the very highest temperature conditions that the siding will ever encounter. As a result, a strip of the apron 52 adjacent to the corresponding edge 43 is revealed. This strip may be larger or smaller, but must always be smaller than the width of apron 52 at all temperature conditions, so that the underlying substrate (the building) remains protected and decoratively concealed.

Depending on the range of temperatures expected, it is advantageous to set the width of the gap 44 between potentially-abutting edges 42, 43 of the shingles or other forms at the extreme ends of the panels 22, as a function of the actual temperature of the panels at the time of its installation. The gap 44 should be wide enough to avoid interference by contact between edges 42, 43 if the temperature should rise. The gap 44 should be small enough to avoid leaving an unsightly wide gap if the temperature should fall. If the gap can be made dependably small, apron 52 can be relatively narrow, thereby saving material.

According to an aspect of the invention, a system is provided for positioning a siding panel 22 or other building component subject to expansion and contraction as a function of temperature, to optimally account for the gap 44 between panels. The siding panel or other building component or element 22 comprises a material having a predetermined thermal expansion characteristic over a temperature range. This characteristic is a product specification that is generally stated by the manufacturer of the siding within tolerance limits. For vinyl or polypropylene siding of the type shown, the coefficient or index of thermal expansion is on the order of $3.5 \times 10^{-5}$ in./in./° F.

Thermal expansion is a well known challenge for the installer of polymer siding and other materials. In order to set the gap between panels at the appropriate width to accommodate changes in the size of the panels, a predetermined gap can be determined or calculated if the temperature of the panel is known accurately. Certain manufacturers supply panels in which a set of hatch marks are molded into the panel material to represent expansion at different temperatures. Such hatch marks are used to choose the gap at which panel elements are mounted, and may be labeled to show recommended gaps at two or more temperatures. However, the temperature of the panels is seldom accurately known and may differ substantially from the ambient air temperature.

Therefore, hatch mark labels, per se, representing nominal spacing as a function of temperature do not show or help to show what gap width is nominal or correct for conditions at the time of panel installation. Subsequent assessment of panel gapping is likewise not possible because one cannot relate the panel gapping dimensions to present panel temperature and/or to an unknown panel temperature at some previous time of installation. Furthermore, even an assembler who works diligently to set joint gaps accurately to the nominal indicated distance for the ambient temperature at the time of installation may experience frustrating thermal expansion problems because the panels individually or as a group may differ substantially from ambient air temperature.

According to one aspect of the invention, the temperature of a panel 22 is sensed during installation (and subsequently) using a temperature sensor that is closely associated with and preferably is directly attached to a panel at or near a joint. According to another aspect, the indicated temperature can be referenced to one or more gap indicating markers, preferably molded into the siding at and/or adjacent to an edge that may interfere with an edge of an abutting panel at a joint, wherein a specific nominal spacing is indicated as a function of panel temperature. According to yet another aspect, the gap spacing as a function of temperature can optionally be built into the temperature sensor, for example expressing the sensed panel temperature as a distance that is used to set the gap. In that case, the temperature indication can be connected graphically to, or numerically referenced to, an adjacent or nearby gap indicating graphic. In this way, the sensed temperature of the panel can be more or less directly converted into a nominal gap for setting thermally affected dimensions, using a visual indicator. The panel temperature is read out spatially or is referenced to spatial indicia.

More particularly, the invention provides a temperature sensing element 62 that presents the sensed temperature as a point in a spatial range 64, or references the sensed temperature to a point in the spatial range, the specific point corresponding to the thermal expansion/contraction characteristics of the panel 22 at the sensed temperature. The invention provides accurate panel temperature gapping because the sensed panel temperature is shown as or cross referenced to a spatial expected thermal expansion attribute. The temperature provides an indicating reference to assess the variation in size and gapping at joint 40 as a function of sensed panel temperature.

Referring to FIG. 1, temperature sensor 62 is provided and is mounted or placed in a position to respond thermally to the panel or other element 22, i.e., to detect the temperature of the panel or other element 22. This temperature may differ from the temperature of the ambient air, for example as in the case when installing siding panels on a sunlit face of a building. Thermal sensor 62 senses the current temperature of the panel 22, for example by placement or mounting in direct thermal contact with the panel, at least for a time sufficient to determine the panel temperature.

Temperature sensor 62 is a form of thermometer but that thermometer is dimensioned to provide a form of indication that can be coordinated with or cross referenced to the thermal expansion properties of the siding material. For example, the temperature can be indicated as a point along a distance between two points that represent respective lengths of material at maximum and minimum temperatures bracketing the present temperature. This point can be indicated directly or indirectly. For direct readout, the temperature can be shown by a visually distinct lightening, darkening, opacity or the like at a point along a scale. It is also possible to provide a scale of sensed temperature as a numeric temperature value, e.g., degrees Fahrenheit or Celsius, etc., or a point on a scale, and then to cross reference that temperature to a point on an expansion scale that is labeled or positioned to enable the temperature to identify a particular point along the distance between points.

Figure 8:
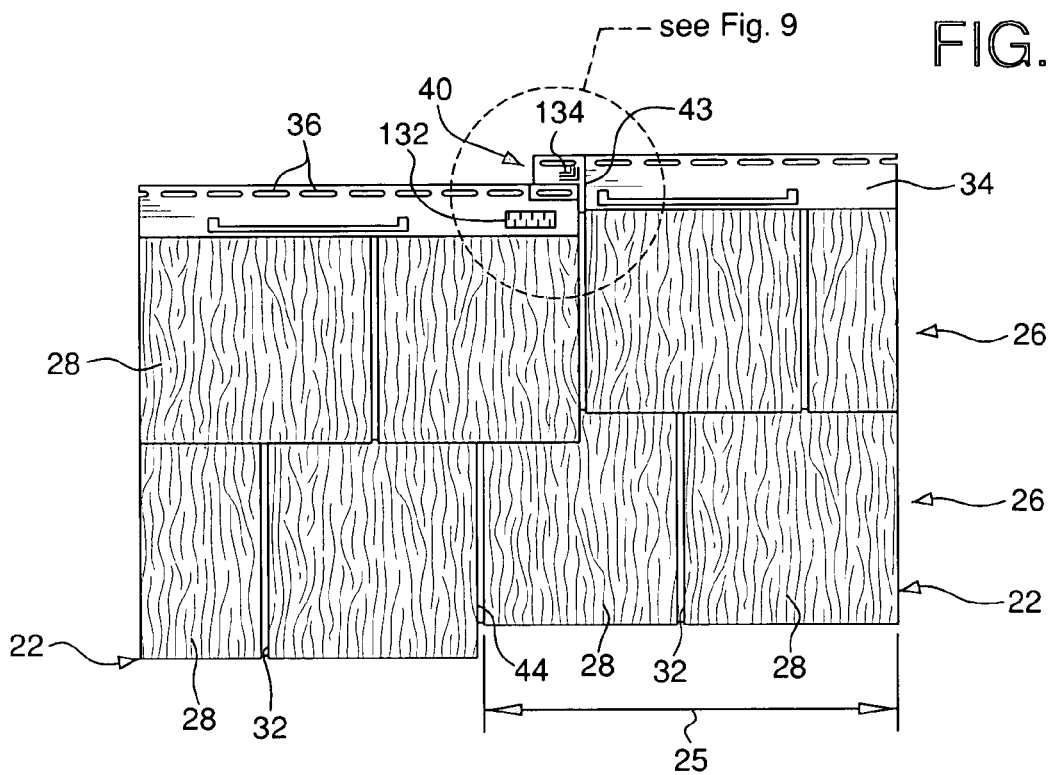
FIG. 8 is an elevation view showing an inventive embodiment wherein a temperature indicator on one panel at a joint provides a temperature measurement to be used in assembly of the joint.
Figure 9:
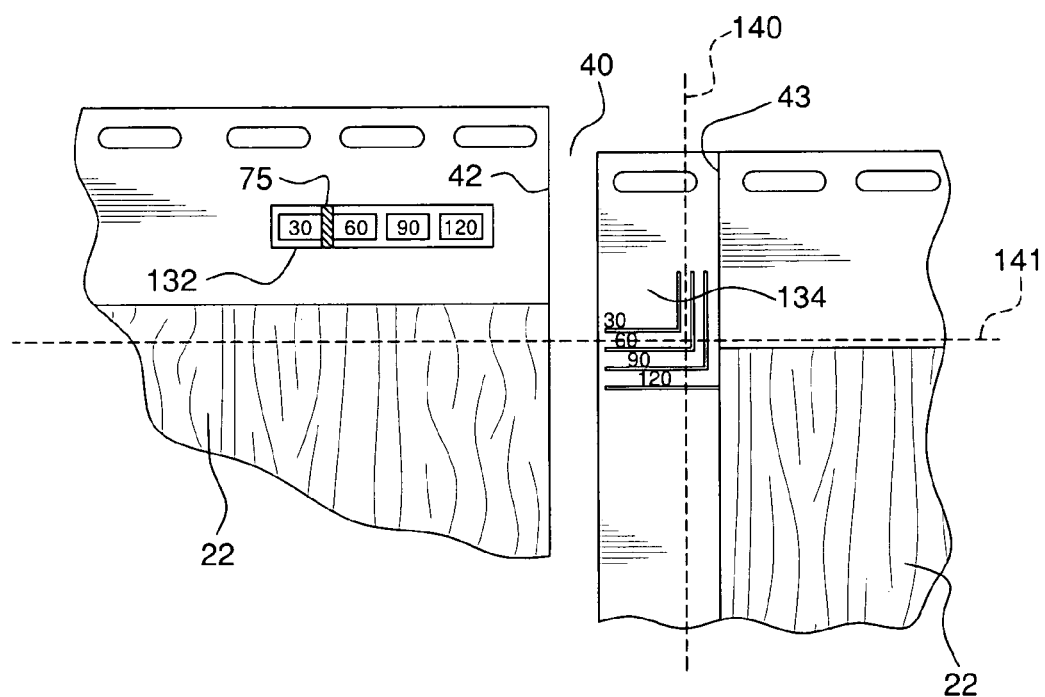
FIG. 9 is an elevation view of the area of the joint shown in FIG. 8, wherein the temperature indicator provides a temperature indication for use with a gap indicator at the other panel at the joint, the gap indicator being labeled for temperatures.

According to an inventive aspect and as shown in FIG. 2, the temperature of the panel 22 is read out spatially in one embodiment, as a characteristic expansion distance or position at a point 75 along a spatial scale or range 64 according to the current sensed temperature, the point in the spatial range 64 of thermal expansion corresponding to the clearance available over a range of siding temperatures. This point can be associated with a numeric temperature label 75, as in the embodiment shown in FIG. 4. In an alternative arrangement, the temperature indication can be graphically connected to indicate an expansion distance as in the embodiment of FIG. 5. In the embodiment of FIGS. 8 and 9, the temperature is indicated by a temperature indicator that reads out a temperature value of one of the panels at a joint, and the installer can refer to indicia that are molded, printed or otherwise provided adjacent to one of the edges 42, 43 to be gapped, the indicia labeling a range of different gap distances by corresponding temperature figures. In that case the installer matches the measured temperature to the indicated gap.

In the embodiments wherein the presentation of sensed panel temperature is graphic, i.e., is presented as a position in a range 64, and also in the embodiments wherein a nominal gap distance is related to a temperature measurement (graphically or by labeling), the precise gap versus temperature is predetermined. The gap represents the extent of expansion of a predetermined thermally expansive body, namely a siding panel or other element that has a known length in the pertinent expansion direction, and is made of a material having a known coefficient of expansion. Therefore, the pitch or incremental distance of the temperature indication scale per degree of temperature according to one aspect provides a temperature expansion measure, or according to another aspect provides a cross reference to a gap scale that likewise provides a measure of expansion as a function of temperature.

This expansion measure is related by visual presentation of the temperature measurement as a point along a range, or by providing an associated indicator or label that associates temperature with the corresponding expansion point along the range. In either case the result is a visual indication of temperature versus distance relationship of a potentially interfering edge, from a reference point on the siding panel or similar building component located at a distance from the edge, and based on the actual sensed panel temperature. Thus, a difference in temperature is represented by a spatial distance or position along the scale or range of temperature 64, but that position is coordinated with thermal expansion of the length of material between the point of the temperature indication and the remote reference point, spaced apart along a direction of elongation that is aligned with the scale of temperature 64.

The basis of the spatial pitch of the temperature is the mathematical product of the coefficient of thermal expansion and the distance between the two reference points in the direction of elongation. One reference point is a predetermined position on the siding panel at a distance from the temperature indication scale, and the other is the spatial point of the indicated temperature or the spatial point that corresponds to the indicated temperature. The spatial point changes with panel temperature so as to provide a gap spacing that changes with panel temperature.

The distance over which thermal expansion affects the gap spacing can be a distance between the potentially interfering edge 42 or 43 and a remote other reference on the panel 22. The remote point that is pertinent to determining the appropriate gap can be different in different embodiments, and might or might not be a point that is fixed relative to the substrate or building wall on which the panel is mounted.

Figure 3:
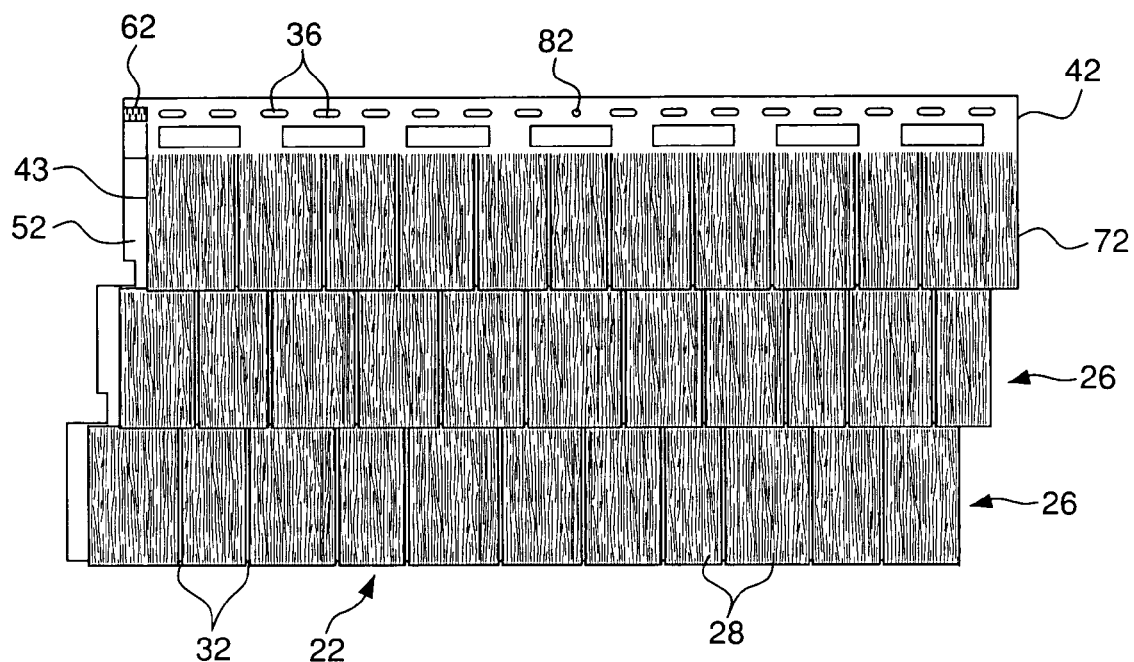
FIG. 3 is an elevation view of a full size siding panel, having a reference opening for fixing a known point on the panel.

For example, the remote reference point can be the opposite or far edge 72 of panel 22 (see FIG. 3). The panel 22, which can have one or plural simulated vertical courses and can be staggered as in FIG. 3, has a nominal size such as four feet or six feet, etc., from the far edge 72 to the near reference point. The near reference point can be one of the potentially interfering edges 42, 43 at a butt joint. The near reference point alternatively can be the spatial position of the temperature indicated on temperature sensor/indicator 62, or can be the spatial position of a temperature indicating hatch mark 134 as in FIG. 9, that is associated with a panel temperature. According to the invention, the distance from the far reference point to the point of the indicated or hatch-marked current temperature (which changes as the temperature changes), corresponds to the extent of expansion and contraction of the siding panel or other building component, according to the thermal expansion characteristic of the panel and the current temperature of the panel.

One aspect of the invention is that if the remote reference point is stationary and the temperature scale of the indicator 62 (e.g., FIG. 2) or the scale of its associated hatch marks 96, 134 (FIGS. 5, 9) defines the near reference point, and further assuming that the layout accurately reflect the coefficient of expansion, then the actively indicated temperature indication or the identified point on the hatching (either of which changes with temperature) remains stationary as the temperature of panel 22 changes and the panel undergoes expansion or contraction. Although absolute accuracy of course is preferred, the invention is also applicable to a similar temperature indication that is only approximate, because it is useful at least that the position of the temperature indication point or the temperature-associated point defining the nominal position of edge 42 or 43, varies less than the extent to which the panel expands or contracts with temperature over the direction of elongation of the panel between the remote and near reference points. This aspect of the invention makes the temperature indicator useful for setting the gap between panels. A smaller gap is indicated as the nominal gap between edges 42, 43 if the panel is relatively warm. A larger gap is indicated when the panel is relatively cool.

The temperature scale or the temperature-associated gap scale hatching are set out to extend and to define incremental gap spacing, in a direction substantially parallel to a direction of elongation, and preferably is co-linear with a line between the remote reference point and the temperature scale or hatch pattern. The higher temperature indication points (which indicate a present state of relative expansion) are indicated on the end of the temperature scale or hatch pattern in the direction that tends to shorten the distance between the reference points (a smaller inter-panel gap). The cooler temperatures (which indicate a present state of contraction) are on the end of the temperature scale or hatch pattern that would lengthen the distance between reference points (a larger inter-panel gap). In other words, the temperature scale and/or hatching is laid out so that the difference in the positions of two unequal indicated temperatures, is opposite from the difference in distance between the reference points that results from that expansion or contraction over that change in temperature. The temperature indications if used directly preferably are pitched by a distance that is equal and opposite to the effect of expansion, and if used indirectly refer to hatch marks that are pitched by that distance.

Reference can be made to the exemplary embodiment of FIG. 2, wherein the temperature scale is spaced to directly identify the position of one edge 42 at a gap. It is understood, however, that the same spacing relationship is used indirectly in FIGS. 5 and 9, where the temperature indication indirectly identifies the position of that edge at the gap in a substantially similar way. The temperature-sensor 62 in FIG. 2, and the scale 64 it encompasses, advantageously are laid out on the apron 52 adjacent to the abutting edge 43 of the endmost shingle (or perhaps some other similar potential point of interference facing along the direction of elongation of a course). The adjacent panel overlaps the apron and its edge 42 is preferably set during installation at a position that reflects the current temperature indication point 75. As shown in FIG. 2, the edge 42 in that case is placed directly on the indicated temperature position 75 shown by temperature sensor 62.

In a given installation, it is conceivable that a skilled installer may decide to provide an extra gap for safety or perhaps to risk a smaller gap than what is recommended (e.g., on the belief that the maximum panel temperature will never be reached). Nevertheless, the invention provides a dependable indication that varies with temperature, of the minimum size gap that will not result in interference if a rise in temperature should cause the panels 22 to expand.

The highest nominal temperature indicated on the temperature scale (on the "H" side in FIG. 2) is a point at or close to the abutting edge 43 of the endmost panel, e.g., siding shingle. The spacing at the highest temperature determines the minimum width gap at the butt joint. In FIG. 2, the indicated temperature 75 is closer to the cooler side ("C") of the temperature scale, and the broken line edge 42 of the adjacent panel is aligned to the indicated temperature 75. If the two panel edges are to have the least possible gap, they should barely abut at the highest temperature ever encountered. For design reasons it may be desirable to have a visible gap at the highest temperature, but in any event, the invention is useful for either or both of setting a gap that will prevent interference at the highest temperature, and also setting a gap that is no larger than necessary. The position of the indicated temperature 75 as shown in FIG. 2 can be relied upon, at any temperature in the scale, as a means to correctly gap the two panels to design specifications.

The invention integrates a temperature sensor 62 and its indicator scale with an expansion distance indicator. Alone or together with associated hatching, the temperature sensor 62 provides a visual indication 75 of the current temperature sensed by the temperature sensor along a distance scale that represents the relative position of the indicated point from a remote reference point at the indicated temperature. The temperature sensor 62 identifies a hatched position or visually relates to an indicated position 75 that moves according to the current temperature by a distance equal to a difference of said expansion and contraction as a function of temperature. In FIG. 2, this result is realized because the pitch of the temperature indication scale (degrees per unit length in the direction of elongation back to the remote reference point) is chosen to equal the thermal expansion rate (length per degree of temperature) over the same length from the remote reference point to the temperature indication point. In other embodiments, the pitch of the hatch scale referenced to temperature is likewise equal to the rate of thermal expansion.

As stated above, the remote reference point can be the far edge 72 of a nominal siding panel as shown in FIG. 3, and the near reference point can be the temperature indication position. It is possible to employ the invention to set a gap between reference points of which one is fixed in position. The reference distance can extend between two points that both are fixed in respective position, such as points on two panels that join to one another with an inter-panel gap. Referring to FIG. 3, one remote reference point can be at a fixed point on the siding panel 22, such as a midpoint hole 82 at which a centrally placed fastener (not shown) is to be received without expansion clearance, thus fixing that hole 82 as a stationary reference position on the substrate (e.g., a building wall). Other fasteners (none being shown) are received in slots 36 that provide clearance in a direction proceeding away from the fixed point, and can be progressively longer proceeding away from the midpoint 82. Alternatively, the slots 36 can be more than long enough, for example providing clearance for expansion to or from any temperature, such that a nail placed at a midpoint of the slot at any installation temperature will never interfere with the end of the slot at another panel temperature. This avoids any issue of interference as to the nails or other fasteners.

The foregoing freedom to provide clearance using slots 36 is due to the fact that the nail strip containing fastener slots 36 is covered by a next higher later-installed panel (not shown) that overlaps the panel shown. Unlike the gaps at butt joints made endwise between panels 22, the overlapping joints are substantially concealed. Nevertheless, the panels experience thermal expansion in all directions parallel to the plane of the substrate. It may be advantageous to employ the present invention not only to set the gaps of butt joints, but also to set a predetermined degree of vertical clearance in the vertical joints made between courses, e.g., using downwardly opening front hook flanges along the nail strip to engage upwardly opening rear hook flanges at the bottom edge of the courses. For example, the hatch marks 134 of FIG. 9 also have a horizontal component that can be spaced to account for differential thermal expansion of siding panel 22 in a vertical direction when installing an overlapping course (see, e.g., reference position 141 in FIG. 9). The invention is discussed primarily with respect to the non-limiting example of expansion in the usually-horizontal direction of elongation between gapped butt joints.

In the embodiment shown in FIG. 3, if a fastener is placed in midpoint hole 82, thermal expansion and contraction of the panel will occur in both opposite directions leading away from the fixed position defined by the central fastener hole. In FIG. 3, it can be assumed that the next adjacent butt jointed panel (not shown) also has a central fixed fastener hole 82 in the same way as the panel 22 shown. The thermal expansion basis in that situation is the distance between the centers of the fixed fastener holes 82 of two abutted panels 22, less the relatively inconsequential dimension of the gap 44 between the panels (see also FIG. 2). Expansion more particularly occurs from the center fixed fastener hole 82 to the edges 42, 43 of each panel, and a contribution is made by both panels 22 that meet at a butt joint. Therefore, the temperature indicator 62 is provided with an incremental temperature/gap pitch that represents thermal expansion over the length of one full panel, end to end, and not only expansion between the central fixed fastener hole 82 and the temperature indication point 75 of the panel on which the temperature indicator 62 and/or its hatching are mounted. In any case, the temperature indication point 75 and a remote reference (in that case the distance between successive holes 82 or the end-to-end length of panel 22) are coordinated with the pitch of the temperature indicator to provide for a precise and correctly set gap. It should be apparent that it would also be possible to provide a fixed fastener hole 82 at some other position, such as at one end of panel 22, with similar results.

One technique for setting the gap between panels 22 is to arrange for the gap to just barely close at the highest expected temperature ever to be encountered, perhaps leaving only minimal if any clearance at that temperature. That technique results in the smallest possible gap over all the temperatures to be encountered, while ensuring sufficient clearance at the highest temperature. It is perhaps preferable due to uncertainty as to the highest temperature to be encountered, and the advisability of providing slightly more clearance than necessary for safety, to space the panels at a slight nominal gap even at the highest temperature. In that case, the gaps 32 between simulated shingles 28 (see also FIG. 1) can have random widths, and some of the simulated gaps 32 will be substantially the same size as the changeable gaps 44 between edges 42, 43, over the range of possible temperatures up or down to the maximum and minimum dimensions expected over the range of temperatures encountered. This advantageously camouflages the gaps between the panels 22, even if the gaps between the panels 22 remain equal (at equal temperatures) and contract or expand as the temperature changes.

The temperature sensor/indicator 62 can be affixed permanently to each siding panel 22, for example as a temperature sensing strip that is bonded to the panel 22 or printed directly on the panel 22 or otherwise fixed integrally or at least adhered permanently. Alternatively, the temperature sensor/indicator 62 can be temporarily placed using a removable adhesive or simply held manually in place. If the temperature sensor is provided for use with a hatching pattern such as hatch pattern 96 in FIG. 5 or pattern 134 in FIG. 9, the hatching pattern likewise can be adhesively affixed or printed or molded integrally into the panel material. Preferably the hatching is placed in the range 64 as a distance scale to identify a nominal temperature-dependent gap spacing, but it is also possible that the hatching could be used merely as a spacing indicator that the installer transfers to the spacing between edges 42, 43 or is later used to assess such spacing at some other arbitrary temperature.

Figure 4:
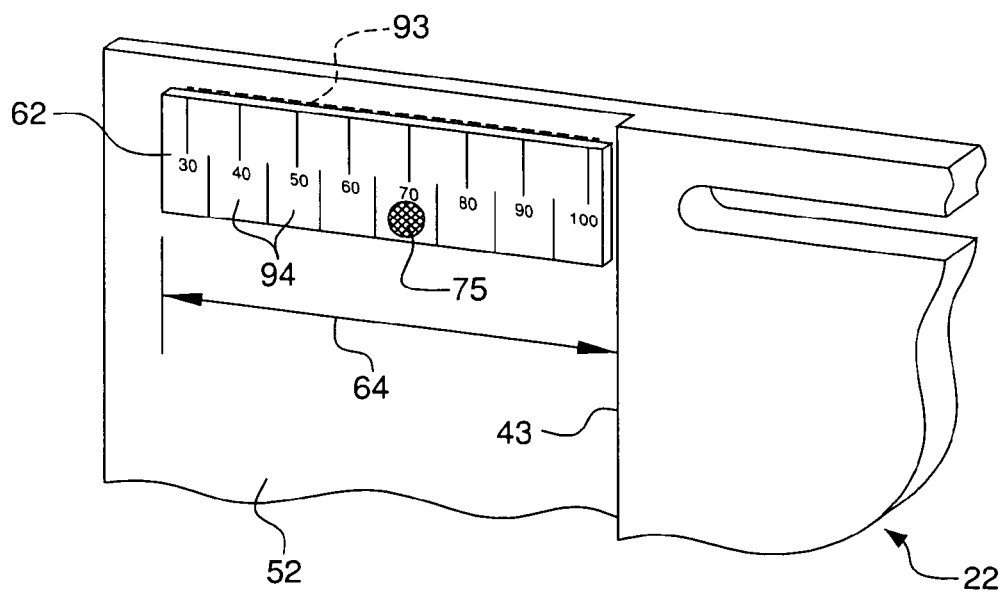
FIG. 4 is a partial perspective showing a temperature indicator according to the invention, attached in position on a siding panel and having a chemical or liquid crystal temperature indication.

In the embodiment shown in FIG. 4, the temperature indicator 62 is a low cost reversible temperature indicator strip of the type used for disposable thermometer strips in medical practice but configured to encompass the range of temperatures to be encountered by the building component (e.g., exterior siding panel), and is affixed to the apron 52 of a panel 22 by an adhesive layer 93. Such temperature indicators are known for reversibly indicating the temperature of containers such as beverage cups (see U.S. Pat. No. 6,386,756—Rice) or baby bottles (U.S. Pat. No. 6,544,614). A reversible temperature indicating label product is available from Dry Pak Industries, Studio City, Calif. Such labels are available to represent temperature by producing visible color variations that occur at a particular sensed temperature, and are available in arrays with threshold temperatures ranging from −30° C. to 120° C. (about −20° F. to 215° F.), which is more than sufficient for the present application. The sensed temperatures are indicated at indicator zones spaced along strips comprising a thin polyester (mylar) web. The zones contain microencapsulated liquid crystal color changing ink that can be specified for change of color at a nominal temperature with an accuracy of ±0.5° C. Used as a method to monitor the current temperature, these labels change colors indicating the actual temperature, for example being labeled to read out a temperature where a green bar appears. Other similar arrangements can also be used.

According to the present invention for example as shown in FIG. 4, the temperature sensor 62 has a plurality of indicator zones 94, one of the zones 75 being visually activated at a given temperature. It is also possible to provide an indicator wherein all of the zones that are above (or below) their individual threshold temperatures become activated.

According to an inventive aspect, the indicator zones 94 of a temperature indicator as described can be spaced or arranged in association with pointing indicia or spaced hatching, at a pitch or spacing distance of distance per degree of temperature that reflects the thermal expansion characteristics of the siding panel 22 or other associated structure or component over a predetermined length. In FIG. 4, the zones 94 are spaced in that way. In the alternative embodiment of FIG. 5, the zones 94 are larger and spaced by a distance greater than the required expansion pitch. In FIG. 9, the indicator 132 provides an indication 75 that is referenced to a hatching pattern 134 wherein a particular point 140 in the hatch pattern corresponds (in this case by numeric label) to the temperature of the panel carrying sensor 132.

The zones can be presented in various ways that are associated or related to spacing. The zones can be defined by lines that are spaced (FIG. 2) or graphically related to lines that are spaced (FIG. 5) or numerically related to such lines (FIG. 9). Other similar possibilities are also apparent and are encompassed by this invention, such as providing temperature indicator zones that have different line lengths or pad sizes (not shown), in particular such that a longer or wider pad becomes visible at a lower temperature and a shorter or narrower pad at a warmer temperature, those dimensions being transferred or compared to the gap between edges 42, 43 as discussed.

The zones can form spaced marks or can correspond to connected hatch marks 96 or labeled marks 134. The spatial range 64 need not extend to or correspond to the edge of indicator 62, and instead the temperature indicator 62 can be spaced from an abutment edge 43 and/or the extreme edge of the panel as in FIG. 4. The indicator 62 can relate to a reference position that is marked on indicator 62 as in the broken line shown in FIG. 5 used to set a gap distance 44 in a range 64 as a function of temperature. The mounting or pitch spacing of the indicator can be unrelated to expansion except by indicating a temperature as in FIGS. 8 and 9 that relates to a gap versus temperature hatching pattern 134.

Figure 5:
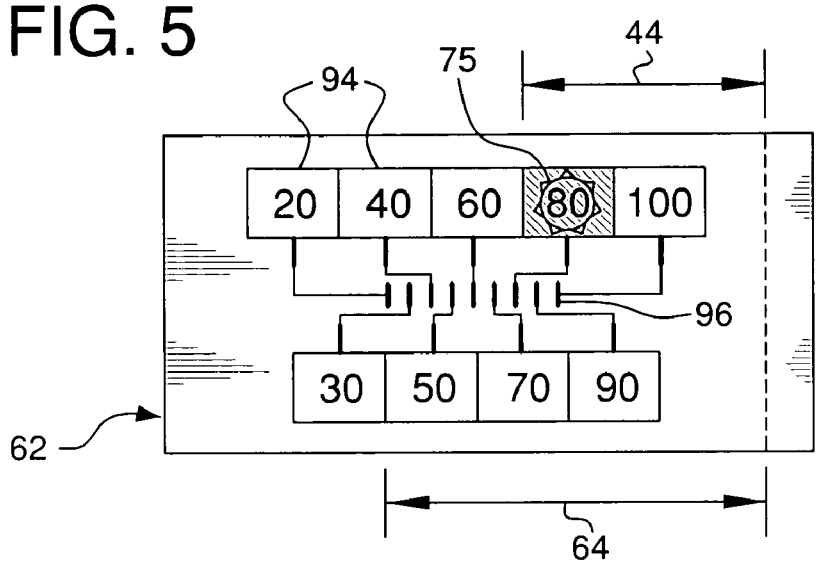
FIG. 5 is an elevation view showing a temperature-to-expansion indicator tool having visible temperature change indicators that are more widely spaced than hatch lines that indicate the associated expansion space.

In the embodiments of FIGS. 4-7, the sensor 62 reads out an associated temperature. In FIG. 5, the spatial hatching 96 represents expansion and can differ in pitch. In FIG. 2, the numerical temperature information is wholly omitted, the corresponding temperature dependent expansion position 75 being visually distinguishable without reference to temperature. In FIG. 9, the temperature indicator 132 is independent of the gap hatching 134 but used to determine a nominal edge position 140. These provisions all enable correct gapping of the panels during installation and/or later assessment of the panel gapping at the same or at different temperatures.

In FIG. 4, the temperature is indicated by a zone and more particularly by an indicator spot 75 that changes appearance when activated, so as to point out one zone 94 in an array of zones. In this embodiment, the temperature indicator 62 comprises an affixed strip. There are fifteen possible zones 94 for temperature indication as shown. It may be sufficient to have fewer zones, for example ten zones representing ten degree increments or five zones representing twenty degrees, etc. The temperature indicating zones can be spread by a distance greater than the associated thermal expansion, if as shown in FIG. 5, the zones are related to expansion.

FIG. 5 shows that the indication areas of the temperature indicator need not be limited to visibly changeable areas that are spaced or pitched by the corresponding expansion distance, provided that the indicators that change visibly are associated with an indicia that is spaced or pitched by the required distance. In the embodiment of FIG. 5, the visible change zones 94, whereon one 75 identifies the current temperature are more widely spaced than the associated distance hatch marks 96. The zones 94 are associated with the distance hatches 96 so as to provide a visible display of a temperature-associated gap or distance. In this example, the nominal gap 44 at the indicated temperature is shown by the depicted arrow. In the other embodiments, the visible part of the temperature indicator zones can be spaced according to the thermal expansion characteristic. In any event, the thermally responsive visually changeable media operate to indicate the current temperature by identifying a point representing a corresponding expansion along the distance scale.

In the different figures, different temperature scales are shown, FIG. 5 encompassing 20 to 100° F. and FIG. 9 encompassing 30 to 120° F. Siding can be specified for different temperatures in part simply by providing the necessary gapping information to accommodated the range of temperatures expected.

The invention is applicable to various building elements including but not limited to exterior wall sheathing and decoration, protective roof surfaces, decks and other applications. An important application of the invention is in the case where the building component is an exterior finishing element subject to thermal expansion, especially a polymer siding panel as shown in FIGS. 1-4, for example of vinyl, polypropylene or another polymeric material. One reference point is a reference position on the panel 22, such as an edge or a fixed point that receives a fastener for mounting the panel (such as hole 82 in FIG. 3). The range of distances is placed for comparison between an edge 43 of the panel and an edge 42 of butt jointed adjacent panel as in FIG. 2, whereby the indicator zones and/or hatching determine a gap dimension 44 between the panel and the adjacent panel at the current temperature. In other applications, the invention can be applied to other elements that need to be positioned to accommodate thermal expansion. The application to polymer materials such as siding is especially apt because such materials are characterized by substantial thermal expansion over the usual ambient temperature range, and are sufficiently flexible that any interference can cause problems that are best avoided.

Figure 6:
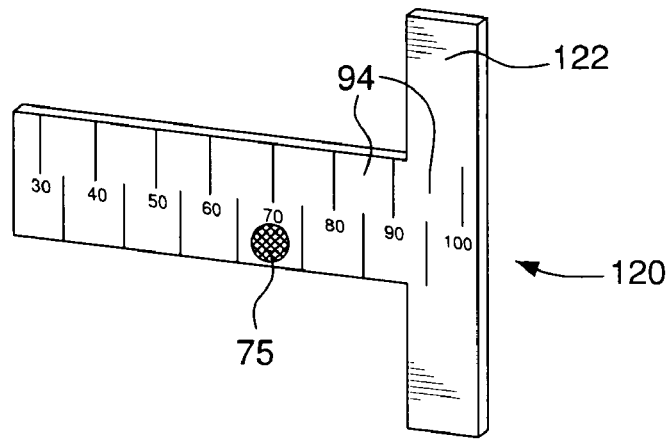
FIG. 6 is a perspective illustration showing a contact thermometer substantially as in FIG. 4, but embodied as a tool for use with siding having corresponding temperature expansion characteristics.

It is possible to affix mylar temperature indicator strips or tags as part of the siding production process. It is also possible to print or otherwise affix markings that visibly change with temperature, directly on the panel material. Alternatively, as shown in FIG. 6, the invention can be applied to a convenience contact temperature tool 120 that is provided as a separate item that the installer can place temporarily at an abutting edge of a gap (e.g., against edge 43 in FIG. 2) when mounting a panel. The temperature indicator tool 120 can have, in addition to the temperature/expansion indicating zones 94, an L-shaped or tee-square form 122 that facilitates placement and alignment against an abutting edge at the gap. The tee-portion can be sized to protrude extend upwardly beyond the nailing strip when indicator 62 is placed as shown in FIG. 1, and easily extracted from between the panels as each next panel is placed and mounted. The temperature indicator need not have an edge reference in the case of FIGS. 8 and 9, wherein the temperature indicator 132 is provided to obtain a numerical temperature readout that is compared or transferred to the hatching 134 nearby.

Figure 7:
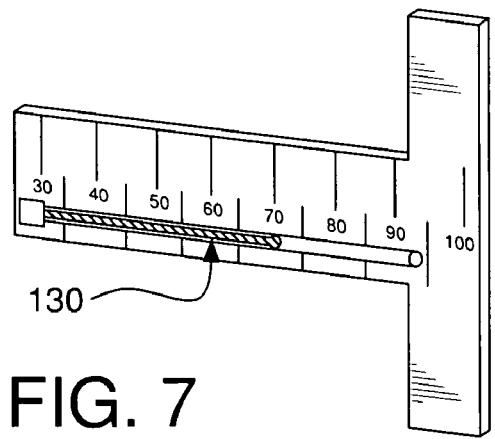

The invention is applicable to other forms of temperature indicators beside thermotropic chemicals, liquid crystal temperature indicators and the like. As shown in FIG. 7, a more traditional form of thermometer comprising a glass tube 130 with a colored thermal expansion liquid can be structured and dimensioned so that expansion with temperature translates to a temperature readout, and optionally to a visible indication of position wherein the temperature readout pitch can correspond to the associated thermal expansion pitch over a predetermined material length. In order to provide the required temperature/distance pitch relationship, the changeable temperature indication (in this case the edge of fluid in thermometer 130) needs to be calibrated with the expansion of a panel over a predetermined pertinent distance such as the length of panels in an expansion direction between ends or from a fixed reference to a potentially interfering edge 43. Other possible thermal expansion devices such as bimetal pointer devices, expanding thermal wax enclosures and the like also are potentially configured for the application. As described with respect to the previous embodiments, any of these can be placed more or less temporarily by manually holding them against a reference position during installation, such as an abutting edge at a gap, or by an adhesive attachment that is easily detached, or by a more permanent connection, not only including adhesive arrangements but also integrally permanent applications such as printing or embedding the visibly changeable material in the siding panel. Also, any of these temperature indicators can provide a numeric indication that is transferred to a pitch defined by hatching.

Insofar as the invention can involve associating visual and spatially correlated thermal expansion indicators, the invention also comprises the method of configuring and installing the siding as described, as well as the combination of elements, namely a thermally expandable element (e.g., a siding panel) a temperature indicator and one or another of the foregoing means for associating temperature change with distance to arrive at a thermal expansion estimation useful for setting or assessing relative position and cross-joint clearance.

The method therefore includes providing a siding panel 22 or similar element that has a predetermined thermal expansion characteristic. This characteristic is such that the siding panel expands and contracts with temperature, thereby producing temperature variations in distance between a reference point and a comparison point on the panel, one such reference point, for example, being one of two edges 42, 43 that may abut and interfere with another surface such as an edge of an adjacent panel. According to the invention, the current temperature 75 of the panel is determined during one of installation of the panel and subsequent assessment or testing. That is, the current temperature of the panel is sensed or measured. A temperature readout can be developed and displayed, for example in degrees Fahrenheit or Celsius, and transferred to a gap indicated by marking or hatching wherein the current temperature is equated to a distance between the reference point and the comparison point at said current temperature, according to the thermal expansion characteristic of the material and taking into account the distance over which such thermal expansion acts, e.g., from a fixed reference point to an edge or between opposite edges of the panel, etc. Alternatively, the temperature readout can be displayed graphically as an indicated point along a range the defines a nominal dimension or position to vary as a function of temperature. Whether the temperature readout is directly presented as a point along a scale. or is referenced to a point on a scale, the scale is calibrated to expansion of a predetermined material length by temperature, and the temperature is that of the panel as opposed to the ambient air or the like. The readout and scale are thus useful to determine appropriate gapping during installation.

Having thereby provided an indication of thermal expansion status and displaying or providing a measure to determine the clearance available for further expansion, it is possible to assess a position of the comparison point relative to the reference point for and the capacity of the panel at that position to accommodate further expansion with heating, preferably without causing interference between edges, or contraction with cooling, preferably without opening undue gaps. Inasmuch as the preferred arrangement shows the present expansion status as a point along a range that might be reached with further heating or cooling, the invention enables assessment of the expansion situation of the panel over the full temperature range because it is known where in its expansion characteristic the panel currently lies, as a function of its sensed temperature. In this way, the precision of an installation can be assessed, even though the panels may presently be at a very different temperature than they were when installed. For example, the observed spacing and the current temperature should correspond to the current position on the scale if the installation has been carried out properly, regardless of a difference in temperature over the interim.

The temperature indication can be shown by providing a changeable indicator at a corresponding expansion position, or a movable indicator that corresponds to expansion position, or an indicator providing a temperature value to be applied to a gapping scale of hatch marks, or some combination of changeable and/or movable parts and associated pointers, lines or other indicia to assist in equating sensed temperature to position.

The invention can be embodied for distribution as a combined siding panel as described, and a temperature indicator as described, namely the temperature indication having a scale spanning a distance between at least two temperature indicating positions that are spaced on the temperature indication scale by a distance that is substantially equal to a distance by which the length of the siding panel between the spaced reference points differs at the two temperatures indicated by the two temperature indicating positions. Alternatively, the invention can be embodied as a temperature/gap measurement instrument or tool that corresponds to the thermal expansion characteristics and length in an direction of elongation, according to the specifications of any corresponding siding panel or other element that complies with such expansion characteristics. In the event that siding material such as polypropylene for injection molding has expansion characteristics that are nearly equal, the temperature-to-expansion tool can be configured for any such siding material having a predetermined nominal reference distance.

In any case, the temperature/expansion indicator tool is associated with a siding panel or with various siding panels that have reference points chosen from the group consisting of an end of the siding panel associated with a joint, an end of the siding panel opposite from an end associated with the joint, a marked point on the siding panel, a fastener reception point on the siding panel, a measured distance from a point on the siding panel, and a structural point in a pattern of the siding panel, wherein the material and there reference distances are such that the tool at least substantially represents the expansion characteristics of the siding by a spatial presentation.

The invention has been disclosed in connection with certain examples and embodiments but is not limited to the particular constructions herein disclosed and shown in the drawings, but also comprises any modifications or equivalents within the scope of the appended claims.

What is claimed is:

1. A siding installation method, comprising providing a first and second building component, one of said components comprising at least one panel characterized by a predetermined thermal expansion characteristic in a range of temperatures over which said panel expands and contracts with temperature, said predetermined thermal expansion characteristic causing a variation in distance between a reference point on said one of the components and a comparison point on the panel;

determining a current temperature of the panel during one of installation and testing, by measuring said current temperature using a temperature sensor that is one of integral with and affixed to the panel;

wherein the current temperature of the panel and the thermal expansion characteristic correspond to a distance between the reference point and the comparison point at said current temperature, and wherein the thermal expansion characteristic is such that a position of the comparison point relative to the reference point changes during subsequent changes in a temperature of the panel; and, affixing said one of the first and second components to a structure at a position relative to an other of the first and second components so as to accommodate the thermal expansion characteristic during said subsequent changes in temperature of the panel.

2. The method of claim 1, wherein the comparison point falls in a range of distances from the reference point and the comparison point corresponds to a point in a corresponding range of panel temperatures according to said thermal expansion characteristic, and further comprising indicating a point on the range of distances corresponding to the current temperature.

3. The method of claim 2, wherein said indicating of the point on the range of distances comprises placing a temperature sensor over the range of distances wherein the temperature sensor has a temperature scale corresponding to a scale of indicator distance that corresponds to the range of distances corresponding to the current temperature sensor.

4. The method of claim 3, wherein the temperature sensor comprises a movable indicator having an expansion material for adjusting an indicated position corresponding to the current temperature.

5. The method of claim 3, wherein the temperature sensor comprises an array of visible indication points activated to represent the current temperature.

6. The method of claim 3, further comprising placing the temperature sensor at a predetermined position at an edge of one of the building components, for indicating a spacing from an edge of an other of said building components that accommodates said predetermined thermal expansion characteristic during the subsequent changes in temperature of the panel, and affixing the first and second components to the structure at such spacing.

7. The method of claim 2, wherein indicating the point on the range of distances comprises referencing a temperature readout value to a position on a hatch pattern having marks placed to represent position versus temperature.

8. An installation method for a roof covering component, comprising providing a first and second building component, one of said components comprising at least one roofing component characterized by a predetermined thermal expansion characteristic in a range of temperatures over which said roofing component expands and contracts with temperature, said predetermined expansion characteristic causing a variation in distance between a reference point on the roofing component and a comparison point on the roofing component;

determining a current temperature of the roofing component during one of installation and testing, by measuring said current temperature using a temperature sensor that is one of integral with and affixed to the roofing component;

wherein the current temperature of the roofing component and the thermal expansion characteristic correspond to a distance between the reference point and the comparison point at said current temperature, and wherein the thermal expansion characteristic is such that a position of the comparison point relative to the reference point changes during subsequent changes in a temperature of the roofing component; and, affixing said one of the first and second components to a structure at a position relative to an other of the first and second components so as to accommodate the thermal expansion characteristic during said subsequent changes in temperature of the roofing component.

9. The method of claim 8, wherein the comparison point falls in a range of distances from the reference point corresponding to a range of component temperatures according to said thermal expansion characteristic, and further comprising indicating a point on the range of distances corresponding to the current temperature.

10. The method of claim 9, wherein said indicating of the point on the range of distances comprises placing a temperature sensor over the range of distances wherein the temperature sensor has a temperature scale corresponding to a scale of indicator distance that corresponds to the range of distances corresponding to the current temperature sensor.

11. The method of claim 10, wherein the temperature sensor comprises an array of visible indication points activated to represent the current temperature.

12. The method of claim 10, further comprising placing the temperature sensor at a predetermined position at an edge of one of the building components, for indicating a spacing from an edge of an other of said building components that accommodates said predetermined expansion characteristic during the subsequent changes in temperature of the roofing component, and affixing the first and second components to the structure at such spacing.

13. The method of claim 9, wherein indicating the point on the range of distances comprises referencing a temperature readout value to a position on a hatch pattern having marks placed to represent position versus temperature.

14. A method for accommodating thermal expansion of building components, comprising providing a building component chosen from the group consisting of a siding component, a wall sheathing component, a roof covering component and a deck component, wherein the building component is characterized by a predetermined thermal expansion characteristic in a range of temperatures over which said building component expands and contracts with temperature, said predetermined expansion characteristic causing a variation in distance between a reference point on said building component and a comparison point on said building component;

determining a current temperature of the building component during one of installation and testing, by measuring said current temperature using a temperature sensor that is one of integral with and at least temporarily affixed to said building component;

wherein the current temperature of the building component and the thermal expansion characteristic correspond to a distance between the reference point and the comparison point at said current temperature, and wherein the thermal expansion characteristic is such that a position of the comparison point relative to the reference point changes during subsequent changes in a temperature of the component; and, affixing a point on the building component to a structure at a position that places the reference point and the comparison point so as to position an edge of the building component between a maximum and a minimum clearance from an edge on at least one of the structure and a second said building component, during thermal expansion and contraction of said building component with subsequent changes in temperature of the building component.

15. The method of claim 14, wherein the comparison point falls in a range of distances from the reference point corresponding to a range of temperatures according to said expansion characteristic, and further comprising indicating a point on the range of distances corresponding to the current temperature.

16. The method of claim 15, wherein said indicating of the point on the range of distances comprises placing a temperature sensor over the range of distances wherein the temperature sensor has a temperature scale corresponding to a scale of indicator distance that corresponds to the range of distances corresponding to the current temperature sensor.

17. The method of claim 16, wherein the temperature sensor comprises an array of visible indication points activated to represent the current temperature.

18. The method of claim 16, further comprising placing the temperature sensor at a predetermined position at an edge of the building component, for indicating a spacing that accommodates said predetermined thermal expansion characteristic during the subsequent changes in temperature of the building component, and affixing the building component to the structure to obtain such spacing between said edge and another location on the structure.

19. The method of claim 15, wherein indicating the point on the range of distances comprises referencing a temperature readout value to a position on a hatch pattern having marks placed to represent position versus temperature.

20. The method of claim 14, further comprising affixing a point on said building component relative to a building structure when the building component is at a current temperature, so as to position an edge on said building component at at least one of a predetermined minimum clearance distance from an adjacent edge of a second said building component when at a higher temperature than the current temperature and a predetermined maximum gap distance from the adjacent edge when at a lower temperature than the current temperature.

* * * * *